US006243437B1

(12) United States Patent
Hu et al.

(10) Patent No.: US 6,243,437 B1
(45) Date of Patent: Jun. 5, 2001

(54) CORONARY CALCIFICATION DETECTION USING RETROSPECTIVE CARDIAC GATING OF IMAGING SYSTEM

(75) Inventors: Hui Hu, Waukesha; Richard E. Kinsinger, Dousman, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/199,511

(22) Filed: Nov. 25, 1998

(51) Int. Cl.$^7$ ........................................................ A61B 6/03
(52) U.S. Cl. .................................................. 378/8; 378/95
(58) Field of Search ............................................ 378/8, 95

(56) References Cited

U.S. PATENT DOCUMENTS

| | | |
|---|---|---|
| 3,952,201 * | 4/1976 | Hounsfield ................................ 375/8 |
| 4,182,311 | 1/1980 | Seppi et al. . |
| 4,206,363 | 6/1980 | Hounsfield et al. . |
| 4,530,109 | 7/1985 | Klausz . |
| 4,547,892 | 10/1985 | Richey et al. . |
| 4,689,670 | 8/1987 | Okazaki . |
| 5,751,782 | 5/1998 | Yoshitome . |
| 5,828,718 | 10/1998 | Ruth et al. . |
| 5,832,051 | 11/1998 | Lutz . |
| 5,991,356 * | 11/1999 | Horiuchi et al. ......................... 378/8 |
| 6,061,423 * | 5/2000 | Hsieh ..................................... 378/15 |

FOREIGN PATENT DOCUMENTS

| | | |
|---|---|---|
| 196 27 166 A1 | 1/1997 | (DE) . |
| 0 370 341 | 5/1990 | (EP) . |
| 0 471 455 | 2/1992 | (EP) . |
| 2036520 | 6/1980 | (GB) . |

OTHER PUBLICATIONS

A. Fiorino, "Electron–beam computed tomography, coronary artery calcium, and evaluation of patients with coronary artery disease," Annals of Internal Medicine 128:839–847, May 15, 1998.
D. Parker, "Optimal short scan convolution reconstruction for fan–beam CT," Med. Phys. (9) 254–257 (1982).
C. Woodhouse, et al., "Coronary Arteries: Retrospective Cardiac Gating Technique to Reduce Cardiac Motion Artifact at Spiral CT," Radiology 204(2) 566–569 (1997).
Y. Arad et al., "The predictive value of electron beam CT of the coronary arteries: 19 month follow–up of 1173 asymptomatic subjects," Circulation 93(11) 1951–3, Jun. 1, 1996.
G. Cowley, "Are you headed for a heart attack despite your low cholesterol? A $400 test makes it easier to find out," Newsweek, Apr. 6, 1998.

* cited by examiner

*Primary Examiner*—Craig E. Church
(74) *Attorney, Agent, or Firm*—Armstrong Teasdale LLP; Christian G. Cabou

(57) ABSTRACT

An imaging system which, in one embodiment, includes a timing algorithm which identifies the proper projection data to be used and a modified halfscan image reconstruction algorithm which provides improved image quality along with the benefits of an enhanced temporal response, is described. In an exemplary embodiment, the timing algorithm includes the steps of determining a diastolic period of a patient's heart and corresponding projection data during the diastolic period. The modified halfscan algorithm includes the steps of identifying redundant data and unequally weighting the data. The resulting images are used for coronary calcification detection.

12 Claims, 2 Drawing Sheets

CORONARY CALCIFICATION DETECTION USING RETROSPECTIVE CARDIAC GATING OF IMAGING SYSTEM

BACKGROUND OF THE INVENTION

This invention relates generally to imaging and more particularly, to coronary calcification detection using an imaging system.

In at least one known imaging system generally referred to as a computed tomography (CT) system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

With known CT system, projection data is collected from a helical or axial scan to generate sequential frames of images of an area, or organ, within a patient. A frame corresponds to a two dimensional slice taken through the imaged object, e.g., the patient. Typically, an operator attempts to minimize the amount of time required to generate each frame to minimize motion related image degradation.

To detect coronary calcification in a patient, images of the patient's heart are generated and reviewed to identify calcium deposits. However, as a result of the movement of the heart and the blood, the heart images may be blurred. The blurring causes difficulty in identifying the areas of calcium deposits.

To reduce the blurring of the images, it is desirable to provide an imaging system which gathers data as the heart motion is minimized. It would also be desirable to provide such a system which weights redundant data having different amounts motion with different weights to improve image temporal resolution.

BRIEF SUMMARY OF THE INVENTION

These and other objects may be attained by an imaging system which, in one embodiment, gathers image data during the relatively motion free period and includes a modified halfscan image reconstruction algorithm which weights redundant data to provide acceptable image quality along with the benefits of an enhanced temporal response. In an exemplary embodiment, the imaging system utilizes an EKG signal to determine a diastolic period of the heart. The diastolic period is then utilized to determine an ending point of the projection data to be used to reconstruct an image. The minimum data duration is then subtracted from the ending point to determine a beginning point of the collected projection data.

In one embodiment, the modified halfscan image reconstruction algorithm unequally weights redundant projection data. More specifically, a higher weight is applied to data collected during a period of less motion of the heart.

The above described imaging system uses projection data during the period of time when heart motion is minimized. In addition, the system unequally weights redundant data having different amounts motion to improve temporal resolution of the images.

DETAILED DESCRIPTION OF THE INVENTION

Figure 1:
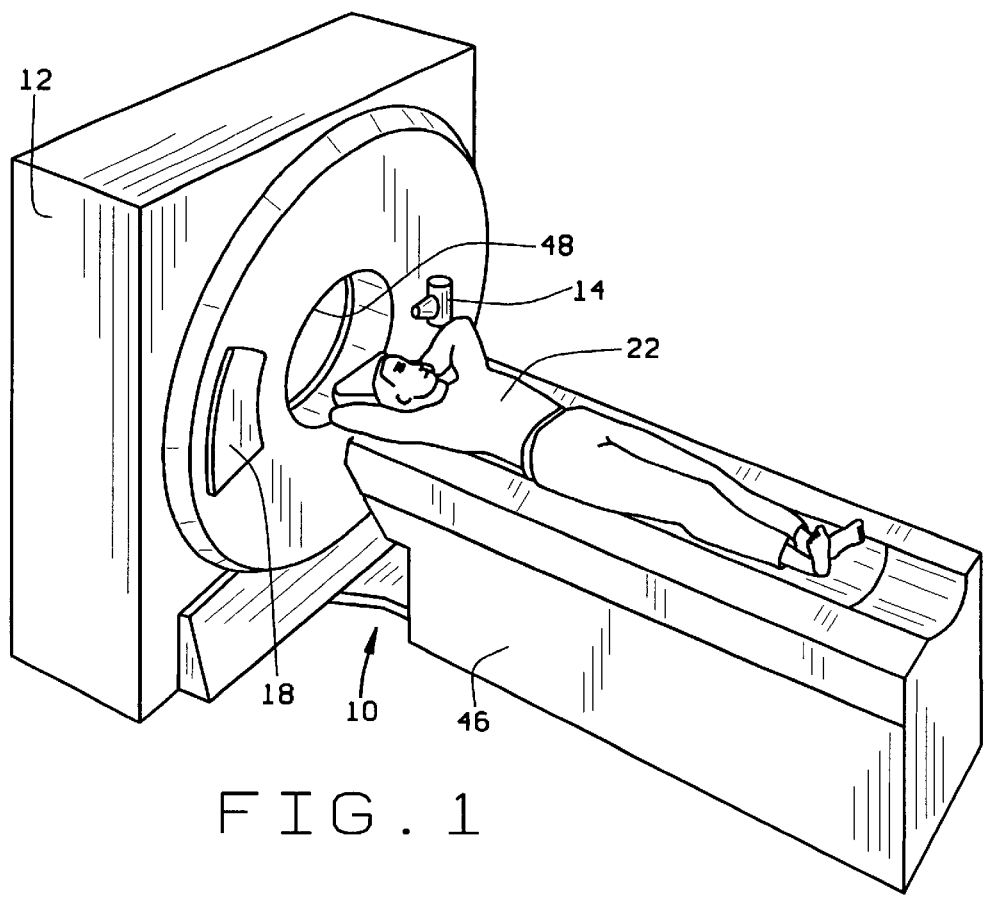
FIG. 1 is a pictorial view of a CT imaging system.
Figure 2:
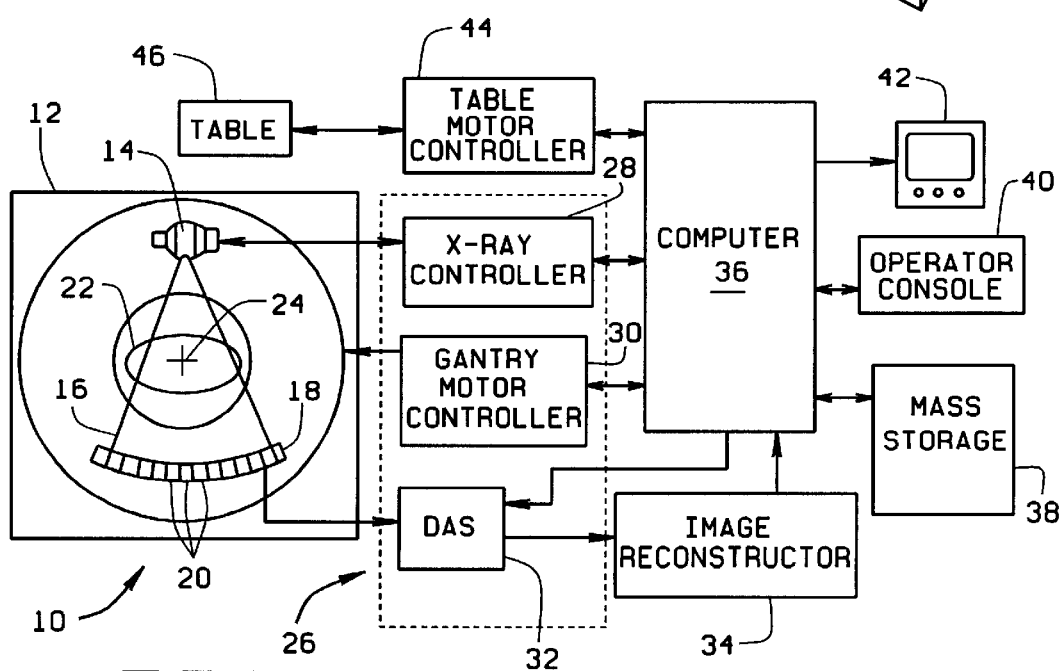
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The timing and image reconstruction algorithms described herein typically are implemented by image reconstructor 34. Such algorithms, however, could be implemented in other components of the imaging system such as in computer 36. Also, it should be understood that system 10 is described herein by way of example only, and the following described timing and image reconstruction algorithms can be practiced in connection with many other types of imaging systems.

In operation, imaging system 10 is configured to generate at least one image of an object in a defined condition, or state. In one embodiment, system 10 is used to generate a series of images of a patient's heart to assist in the detection of coronary artery calcification (CAC). Specifically, after collecting projection data and corresponding heart data, system 10 generates image data by selecting a portion of the projection data corresponding to a relatively motion free period of the heart. The selected projection data is then weighted in accordance with a halfscan weighting function.

Figure 3:
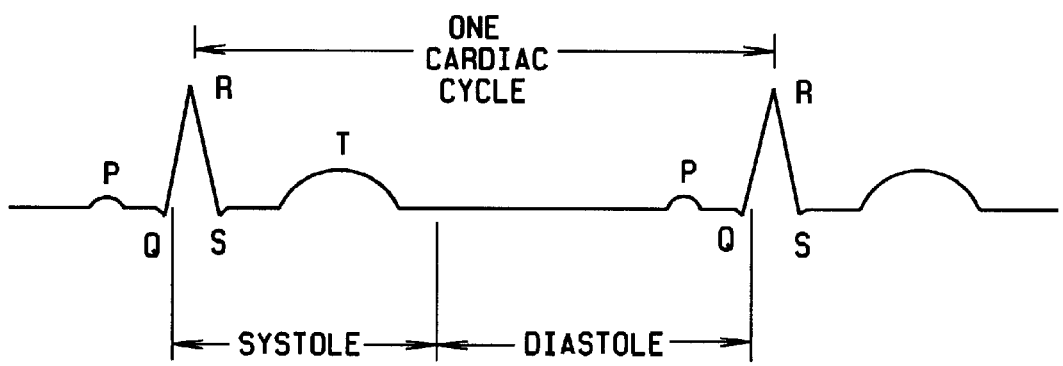
FIG. 3 is an EKG signal waveform.

More specifically and in one embodiment, system 10, utilizing a timing algorithm, detects the condition, or state, of the heart of patient 22 by measuring, or determining, the state of an electrocardiography (EKG) signal. The EKG signal is coupled to system 10, e.g., computer 36, and represents the electrical activity associated with the heart muscle versus time. Referring to FIG. 3, the EKG signal waveform illustrates one cardiac cycle including a systole condition, or period, and a diastole condition, or period of the heart. The portion of the EKG signal which is labeled Q, R and S is referred to as the QRS complex, in which the R-feature, or R-wave, is the most prominent, highest amplitude, feature of the entire EKG signal. The cardiac cycle is typically defined as beginning with a R-wave and continuing until the occurrence of the next R-wave.

Heart functions are characterized by two distinct periods called systole and diastole. In systole, the heart muscle is contracting the volume of the left ventricle to pump the contents out through the aortic valve. During the diastole, or diastolic period, the left ventricle is filling through the mitral valve. At the end of the systole, the left ventricle has its smallest volume since it has been contracted to pump blood out. The end of the diastole is the point at which the left ventricle has its largest volume since it is filled with blood ready to be pumped out. During the diastolic period the heart is relatively motion-free allowing images generated from data collected during this period to be clearer as a result of the limited movement.

Particularly, corresponding projection data and heart data, i.e., the EKG signal, specifically, the R-wave, are continuously collected using system 10. In one embodiment, projection data corresponding to the heart being in a diastolic condition, as determined by the state of the EKG signal, is used in image reconstruction. More specifically, as a result of the cardiac cycles being fairly constant, the R-wave portion of the EKG signal is utilized to determine an end of data period, or time, to be used in reconstruction. The end of data point defines the end of the portion of projection data to be used and is determined with respect to the time when the R-wave transitions from a first state, e.g., a low voltage level, to a second state, e.g., a value above a defined, or selected, voltage level. The R-wave second state helps to indicate the end of the diastolic condition of the heart.

A portion of the data collected using system 10 is then selected based on certain scan variables, including the scan speed, using, for example, computer 36. A begin, or start, of data point, or time, to be used in reconstruction is then determined by subtracting a minimum data duration from the end of data period.

For example and in one embodiment, for a 1 second gantry rotational speed scan, the minimum data duration is approximately 0.6 second. If the end of data point is designated as time E, the begin of data point equals the quantity (E-0.6). In one embodiment, the value of E is derived relative to the R-wave transition, i.e., a low to high level transition, by adding or subtracting an offset, or error.

Figure 4:
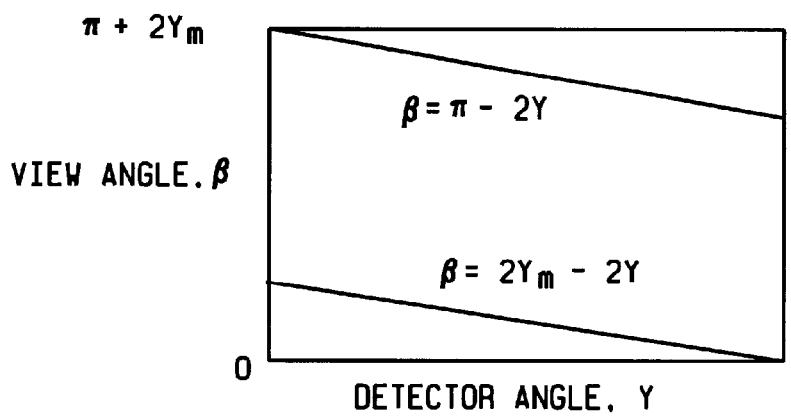
FIG. 4 is a radon space diagram for a modified halfscan.

After the projection data to be used is determined, object images are generated using the halfscan weighting function, or algorithm. As shown in FIG. 4 illustrating a Radon space representation of the projection data, the upper and lower shaded triangles represent the beginning and ending portions of the projection data. More specifically, the upper and lower shaded triangles represent a respective first data set and second data set of redundant data. To improve temporal resolution of the images and reduce motion susceptibility, a modified halfscan algorithm is utilized. In one embodiment, the modified halfscan algorithm unequally weights the projection data. More specifically, after identifying the redundant data, the modified halfscan algorithm applies unequal weights to the redundant data. Particularly, a first weight is applied to the first data set and a second weight is applied to the second data set. More specifically and in one embodiment, where the first data set includes data experiencing less motion of the heart, the first weight is greater than the second weight.

After weighting the projection data in accordance with the modified halfscan algorithm, the images are generated in accordance with known image generation algorithms, e.g., filtered backprojection. Utilizing the images, an operator may identify, or detect coronary artery calcification of the heart of patient 22.

The above described imaging system uses projection data during the period of time when the heart motion is minimized. In addition, the system unequally weights redundant data having different amounts motion to improve resolution of the images. As a result of the images being less motion susceptible, coronary artery calcification detection is improved.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims.

What is claimed is:

1. A method for generating an image of an object using data collected in a computed tomography imaging system, said system comprising an x-ray source, an x-ray detector aligned with said x-ray source, and a display for displaying image reconstructed from data collected by said detector, said method comprising the steps of:

determining a defined condition of the object;

scanning the object with the computed tomography imaging system to obtain projection data of the object;

selecting a portion of the projection data obtained while the object is in the defined condition;

weighting projection data in accordance with a halfscan weighting function; and generating image data for the defined condition from the weighted data, and wherein selecting a portion of the projection data obtained while the object is in the defined condition comprises the steps of:

determining an end of data point;

determining a minimum data duration; and determining a begin data point utilizing the determined end of data point and the determined minimum data duration.

2. A method in accordance with claim 1 wherein the object is a patient heart, and wherein determining the defined condition of the object comprises the step of determining a diastolic condition of the heart.

3. A method in accordance with claim 2 wherein the imaging system is coupled to an electrocardiography signal, and wherein determining the diastolic condition of the heart comprises the step of determining a R-wave state of the electrocardiography signal.

4. A method in accordance with claim 3 further comprising the step of using the R-wave to determine the end of data point as an end of the diastole period.

5. A method in accordance with claim 1 wherein the identified condition is a condition of minimum motion of the object, and weighting the projection data in accordance with the halfscan weighting function comprises the step of identifying redundant data; and wherein the halfscan weighting function is a modified halfscan weighting function that unequally weights the identified redundant data in accordance with an amount of motion of the object.

6. A method in accordance with claim 5 wherein the redundant data comprises a first data set at a beginning portion of the selected projection data and a second data set at an ending portion of the projection data, and wherein to unequally weight the identified redundant data, said method further comprises the step of:

applying a higher weight to either the first data set or the second data set depending upon which was obtained during a period of lesser motion of the object.

7. A computed tomography system for generating an image of an object, said system comprising an x-ray source, an x-ray detector aligned with said x-ray source, and a display for displaying image reconstructed from data collected by said detector, said system configured to:

determine a defined condition of an object;

select projection data during the defined condition;

weight projection data in accordance with a halfscan weighting function; and generate image data for the defined condition from the weighted data, and, wherein to collect projection data during the defined condition, said system is configured to:

determine an end of data point;

determine a minimum data duration; and determine a begin data point utilizing said determined end of data point and said determined minimum data duration.

8. A system in accordance with claim 7 wherein the identified condition is a condition of minimum motion of the object, and to weight the projection data in accordance with the halfscan weighting function, said system is configured to identify redundant data; and wherein the halfscan weighting function is a modified halfscan weighting function that unequally weights the identified redundant data in accordance with an amount of motion of the object unequally weight the identified redundant data in accordance with an amount of motion of the object.

9. A system in accordance with claim 8 wherein the redundant data comprises a first data set at a beginning portion of the selected projection data and a second data set at an ending portion of the projection data, and wherein to unequally weight the identified redundant data, said system is configured to:

apply a higher weight to either the first data set or the second data set depending upon which was obtained during a period of lesser motion of the object.

10. A system in accordance with claim 7 wherein the object is a patient heart, and wherein to determine the defined condition of the object, said system is configured to determine a diastolic condition of the heart.

11. A system in accordance with claim 10 wherein the imaging system is coupled to an electrocardiography signal, and wherein to determine the diastolic condition of the heart, said system is configured to determine a R-wave state of the electrocardiography signal.

12. A system in accordance with claim 11 configured to use the R-wave state of the electrocardiography signal to determine the end of data point as an end of the diastole period.

* * * * *